United States Patent [19]

Heinsohn

[11] Patent Number: 5,233,080
[45] Date of Patent: Aug. 3, 1993

[54] PREPARATION OF N-ACYLAMINOMETHYLPHOSPHONIC ACIDS AND AMINOMETHYLPHOSPHONIC ACIDS

[75] Inventor: George E. Heinsohn, Elkton, Md.

[73] Assignee: E. I. Du Pont de Nemours and Company, Wilmington, Del.

[21] Appl. No.: 951,626

[22] Filed: Sep. 25, 1992

[51] Int. Cl.$^5$ ................................ C07F 9/30
[52] U.S. Cl. ................................ 562/15
[58] Field of Search ........................ 562/15

[56] References Cited

U.S. PATENT DOCUMENTS

| 4,470,191 | 9/1984 | Cottrell et al. | 29/576 |
| 4,657,705 | 4/1987 | Miller et al. | 562/17 |
| 4,851,159 | 7/1989 | Fields et al. | 562/17 |
| 5,041,627 | 8/1991 | Baysdon et al. | 562/16 |

FOREIGN PATENT DOCUMENTS 0186648 12/1985 European Pat. Off. .
9203448 5/1992 PCT Int'l Appl. .

*Primary Examiner*—José G. Dees
*Assistant Examiner*—Samuel Barts

[57] ABSTRACT

N-acylaminomethylphosphonic acids having the formula $RCO-NH-CH_2-P(=O)(OH)_2$, where R is a non-interfering organic radical, are prepared by (A) combining a solution of a carboxamide, $RCO-NH_2$, paraformaldehyde and phosphorous acid in an anhydrous solvent with a carboxylic acid anhydride, e.g., acetic anhydride, or (B) combining a solution of the carboxamide and paraformaldehyde in an anhydrous solvent with a solution of the carboxylic acid anhydrid and phosphorous acid in an anhydrous solvent, followed by heating the resulting solution to complete the reaction. The N-acylaminomethylphosphonic acids can be hydrolyzed to aminomethylphosphonic acid.

16 Claims, No Drawings

PREPARATION OF N-ACYLAMINOMETHYLPHOSPHONIC ACIDS AND AMINOMETHYLPHOSPHONIC ACIDS

BACKGROUND OF THE INVENTION

1. Field of the Invention

This invention relates to a process for the preparation of N-acylaminomethylphosphonic acids. More particularly, the invention relates to the production of N-acylaminomethylphosphonic acids from carboxylic acid amides, a suitable formaldehyde source, phosphorous acid, and a carboxylic acid anhydride in the absence of halogenated reactants, whereby possible contamination of the reaction mixture by carcinogenic halomethylethers is avoided.

The N-acylaminomethylphosphonic acids are intermediates to aminomethylphosphonic acid, and both classes of compound are intermediates to N-phosphonomethylglycine, as is disclosed in U.S. Pat. Nos. 5,041,627, 4,470,191 and 4,851,159 and in European Patent Application 186,648.

N-phosphonomethylglycine, commonly known as glyphosate, is a broad spectrum phytotoxicant or herbicide useful in controlling the growth of a wide variety of plants.

2. Related Prior Art

Numerous methods are known for the preparation of N-acylaminomethylphosphonic acids. Various such methods are reviewed in the above-referenced U.S. Pat. No. 5,041,627 by Baysdon and Fields, which patent is hereby incorporated herein by reference. Patentees Baysdon and Fields teach that prior processes that involve reaction of N-methylolcarboxamide intermediates suffer from low yields or problems associated with handling unstable methylol derivatives. They accordingly propose and claim a process for the preparation of N-acylaminomethylphosphonic acids which comprises bringing together under substantially anhydrous reaction conditions a suitable carboxamide and paraformaldehyde, thereafter adding phosphorous trihalide to form a reaction mixture, heating the reaction mixture and adding water to form the desired N-acylaminomethylphosphonic acid.

Whatever the merits of the disclosed process, the use of phosphorous trihalide, e.g., phosphorous trichloride, entails the serious disadvantage that there is the likelihood of producing reaction mixtures contaminated with carcinogenic halomethylethers.

In this connection, Kleiner in WO/03448, published May 3, 1992, states that processes involving treatment of N-hydroxymethylamides with phosphorous trichloride followed by hydrolysis with hydrochloric acid are highly disadvantageous in that they produce the carcinogenic bischloromethylether as a byproduct. Kleiner proposes instead to prepare aminomethylphosphonic acid by reaction of a suitable N-hydroxymethylcarboxamide with phosphorous acid in the presence of at least equimolar quantities of acetic anhydride to form a reaction product (undescribed) followed by heating the reaction product with large quantities of water at elevated temperatures for extended periods of time.

The Kleiner process itself suffers in that it requires the use of preformed N-hydroxymethylcarboxamides as starting materials, and large excesses of water at elevated temperatures for long periods of time in order to obtain the desired aminomethylphosphonic acid.

Thus, a need exists for a N-acylaminomethylphosphonic acid process that avoids the need to use a preformed N-hydroxymethylcarboxamide starting material and eliminates the possibility of the formation of undesirable halomethylether byproducts. A need also exists for an improved process for hydrolyzing N-acylaminomethylphosphonic acid to aminomethylphosphonic acid.

Another aspect of the invention comprises an improved hydrolytic process wherein the N-acylaminomethylphosphonic acids are effectively and efficiently hydrolyzed to aminomethylphosphonic acid by treatment with dilute(3-10% by weight) mineral acid, e.g., hydrochloric or sulfuric, under relatively mild conditions of temperature and time, e.g., 100° to 130° C. in less than 4 hours, in marked contrast to prior art procedures involving concentrated acid (e.g., concentrated (37%) hydrochloric acid) for 16 hours at reflux or water alone at 200° C. for 20 hours.

SUMMARY OF THE INVENTION

N-acylaminomethylphosphonic acids are prepared by controlled reactions of a suitable carboxamide, paraformaldehyde, phosphorous acid and a carboxylic acid anhydride in the substantial absence of reactive halogen compounds.

In one embodiment, a substantially anhydrous homogeneous solution of the carboxamide, paraformaldehyde, phosphorous acid and a substantially anhydrous carboxylic acid, e.g., acetic, in a substantially anhydrous organic solvent is treated with the anhydride at controlled temperatures to form a reaction mixture, the reaction mixture is heated to complete the formation of the N-acylaminophosphonic acid, and the phosphonic acid product is recovered from the reaction mixture.

In another embodiment, a solution (reaction mixture) of the anhydride and the phosphorous acid in a substantially anhydrous organic solvent is mixed with a solution of the carboxamide, paraformaldehyde and a substantially anhydrous carboxylic acid, e.g., acetic, in an anhydrous organic solvent, the solutions are brought together under controlled conditions of mixing and temperature to form a final reaction mixture, the reaction mixture is heated to complete the formation of the desired N-acylaminomethylphosphonic acid, which is then recovered from the heated reaction mixture.

The process of this invention uses readily available starting materials and provides the N-acylaminomethylphosphonic acids in good yields essentially free of bis-chloromethylether and other noxious halogenated byproducts.

The N-acylaminomethylphosphonic acids are readily convertible to aminomethylphosphonic acid, $NH_2-CH_2-P(=O)(OH)_2$, by methods known to the art.

DETAILED DESCRIPTION OF THE INVENTION

The N-acylaminomethylphosphonic acids are basically composed of units derived from a suitable carboxamide, a formaldehyde source and phosphorous acid, each substantially anhydrous.

Suitable carboxamides have the formula $RCO-NH_2$, where R is a non-interfering organic radical. By "non-interfering" radical is meant one that does not interfere with either the process of the invention or the subsequent removal of the acyl groups, as by hydrolysis, to form aminomethylphosphonic acid, intermediate to N-phosphonomethylglycine. R substituents that do not interfere with the reaction leading to the N-acylaminomethylphosphonic acids and do not significantly hinder their hydrolytic cleavage to aminomethylphosphonic acid are well known in the art, and include such radicals as: lower alkyl, notably methyl and ethyl; benzyl; phenyl; and benzyl and phenyl substituted with lower alkyl, lower alkoxyl or nitro groups. Acetamide is the preferred carboxamide for its ready availability and low cost.

The paraformaldehyde source, which also should be substantially anhydrous, is conveniently and preferably formaldehyde.

The substantially anhydrous organic solvent employed herein may be a protic or aprotic, represented by glacial alkanoic acids, such as acetic and propionic, alkanonitriles, such as acetonitrile and propionitrile, and ethers such as tetrahydrofuran and dioxane. Preferred are glacial acetic acid and acetonitrile, in particular the nitrile and its mixtures with the acetic acid, more particularly such mixtures wherein the nitrile predominates, as it has been found the selectivity of the reaction to produce the N-acylaminomethylphosphonic acid is improved in the presence of the nitrile solvent component. The quantities of solvent employed can vary widely provided there is sufficient solvent to provide substantially homogeneous solutions of the reactants where required as described below.

The carboxylic acid anhydride is preferably acetic anhydride, although other carboxylic anhydrides may be employed such as propionic acid anhydride and benzoic acid anhydride. At least a molar proportion of the anhydride is employed for each mole of the carboxamide and phosphorous acid employed with generally not more than two moles per mole of each of these other ingredients (reactants) needed.

In the process of this invention, the carboxamide and paraformaldehyde are combined, as by mixing, under substantially anhydrous conditions, conveniently by adding them in substantially equimolar quantities to an anhydrous organic solvent, preferably protic, such as glacial acetic or other carboxylic acid, and effecting dissolution by heating if necessary to form a substantially homogeneous solution. For example, a mixture of acetamide, paraformaldehyde and solvent quantities of glacial acetic acid or a mixture of acetic acid and acetonitrile is heated at a temperature in the range of about 50° to about 100° C. for 10 to 40 minutes to form a substantially homogeneous solution. The time, temperature and solvent quantities required to form a solution of acetamide (or other carboxamide) and paraformaldehyde in other substantially anhydrous organic solvents can readily be determined by trial by those skilled in the art.

In one embodiment, phosphorous acid is added to the solution of the amide and paraformaldehyde in the organic solvent to form a solution of all three ingredients, generally at a temperature below about 50° C. Dissolution of phosphorous acid in a solution based on acetonitrile or anhydrous acetic acid, i.e., glacial acetic acid, is endothermic, which aids in lowering the temperature further. The resulting solution is preferably lowered, by further cooling if necessary, to about 20° C., generally between 10° and 20° C., and is treated with acetic anhydride (or with other suitable anhydride, described above), in amounts providing at least an equimolar proportion for each of the carboxamide and phosphorous acid components. The addition of the anhydride is best conducted in portions so as to keep the temperature below about room temperature, preferably 20° C. with lower than 10° or 15° C. not generally needed. The resulting solution (reaction mixture) is heated to temperatures in the range of about 60° to 120° C., more usually about 80° to 100° C., and held at such temperatures until the formation of the N-acylaminophosphonic acid is substantially complete, which may require from one to several hours. For example, with such reactive mixture derived from acetamide, paraformaldehyde, phosphorous acid and acetic anhydride in a solvent such as glacial acetic acid or acetonitrile or a mixture of the two wherein acetonitrile predominates, heating at about 95° C. for 2 hours generally suffices. The optimum times and temperatures required to complete the reaction with other amides are readily determined by trial. Also, depending on the nature of the amide, the anhydride and the solvent and its quantity, the formation of the desired N-acylaminomethylphosphonic acid in substantial amounts can sometimes be followed during the heating period by the appearance of cloudiness in the solution (reaction mixture).

Recovery of the N-acylaminomethylphosphonic acid product from the reaction mixture can be accomplished simply by distilling at reduced pressures to remove (and recover) the solvent and leave the product, whose composition can be established by $^1H$ nmr spectroscopy in $D_2O$ solvent or by any convenient means.

In another embodiment, phosphorous acid and the carboxylic anhydride, normally acetic anhydride, are combined, preferably in a solvent described above and more preferably in glacial acetic acid or acetonitrile or a mixture thereof, in particular such mixture wherein acetonitrile predominates. Since the resulting composition (solution) is to be subsequently combined with a composition comprising a carboxamide and paraformaldehyde, the quantity of the anhydride should be sufficient to provide at least an equimolar amount of each of the phosphorous acid used above and the carboxamide to be mixed therewith subsequently.

The combination of the anhydride with the phosphorous acid, which is believed to form a mixed anhydride compound of the two acid moieties involved, is preferably carried out at relatively low temperatures, generally about 20° C., more usually between about 10° and 30° C.

The resulting solution comprising the anhydride and the phosphorous acid (and/or reaction product thereof) is then mixed with a substantially equimolar solution of a carboxamide and paraformaldehyde in a solvent described above, preferably in glacial acetic acid, acetonitrile or a mixture thereof, in particular a mixture wherein acetonitrile predominates. The mixing of the two solutions is preferably carried out at temperatures below about 20° C., more usually between about 10° and 30° C., and forms a reaction mixture.

The reaction mixture is then heated, as described above, at temperatures of about 60° to 120° C. and held at such temperature until the formation of the N-acylaminomethylphosphonic acid is substantially complete, and the N-acylaminomethylphosphonic acid is recovered therefrom as described above.

The Example below further illustrates the invention and is not to be construed as limited the scope thereof.

EXAMPLE

A 200 ml flask is charged with 95% paraformaldehyde (3.32 g, 105 m mole), acetic acid (6.3 g, 105 m mole), acetamide (6.2 g, 105 m mole), and acetonitrile (45 ml) and heated to 80° C. for 35 minutes. The mixture is cooled to 20° C. and phosphorous acid (8.45 g, 97%, 100 m mole) added. Dissolution of the phosphorous acid is endothermic, cooling the reaction mixture to 15° C. Acetic anhydride (35.5 g, 348 m mole) is added dropwise using external cooling to keep the temperature at about 20° C. The resulting clear solution is heated to 95° C. for 2 hours. After about 1.5 hours, the reaction mixture turns cloudy. The pressure is then lowered to approximately 100 mm Hg and solvent distilled (~60 g), leaving a clear liquid. Analysis by $^1$H nmr spectroscopy in $D_2O$ solvent indicates the presence of 11.2 g (72.4%) N-acylaminomethylphosphonic acid. This material can be readily converted to aminomethylphosphonic acid by methods known in the art.

Preferably, the N-acylaminomethylphosphonic acid is hydrolyzed in accordance with another aspect of this invention, which comprises heating the reaction product at reflux with 5% $H_2SO_4$ or 5% HCl for about 3 hours. The course of the hydrolysis may be followed by $^1$H nmr spectroscopy in $D_2O$ solvent.

I claim:

1. A process for the preparation of N-acylaminomethylphosphonic acid having the formula RCO—NH—CH$_2$—P(=O)(OH)$_2$, where R is a non-interfering aliphatic or aromatic radical, which comprises the steps:
   (a) combining under substantially anhydrous conditions
      (i) a carboxamide having the formula RCO—NH$_2$, where R is as defined above,
      (ii) paraformaldehyde, and
      (iii) phosphorous acid
   in a substantially anhydrous organic solvent for ingredients (i), (ii) and (iii) in an amount and at a temperature effective to form a substantially homogeneous solution;
   (b) mixing said solution at about room temperature or below with at least a molar proportion based on the carboxamide of a carboxylic acid anhydride and, in addition, at least a molar proportion of the anhydride based on the phosphorous acid, the mixing of the anhydride with the solution being controlled to maintain the temperature of the resulting mixture at below room temperature and to produce a substantially clear solution;
   (c) heating the resulting solution to a temperature below its decomposition temperature effective to result in the formation of an N-acylaminomethylphosphonic acid, RCO—NH—CH$_2$—P(=O)(OH)$_2$, where R is as defined above, and
   (d) recovering said N-acylaminomethylphosphonic acid from the solution.

2. The process of claim 1 wherein substantially equimolar proportions of the carboxamide, paraformaldehyde and phosphorous acid are employed.

3. The process of claim 1 or 2 wherein the solvent of step (a) is a lower alkanoic acid alone or mixed with a lower alkanonitrile.

4. The process of claim 3 wherein the acid is acetic acid and the nitrile is acetonitrile.

5. The process of claim 4 wherein the solvent consists essentially of a major proportion of acetonitrile and a minor proportion of acetic acid.

6. The process of claim 1 or 2 wherein the carboxylic anhydride is an anhydride of a lower alkanoic acid.

7. The process of claim 6 wherein the anhydride is acetic anhydride.

8. The process of claim 5 wherein dissolution of the ingredients (i), (ii) and (iii) in the organic solvent in step (a) is effected at a temperature of from about 50° to 100° C.

9. The process of claim 8 wherein the solution in step (c) is heated at a temperature of from about 80° to 100° C.

10. The process of claim 2 wherein the addition of the anhydride in step (b) is conducted at a temperature between about 10° and 30° C.

11. The process of claim 10 wherein the anhydride is acetic anhydride.

12. The process of claim 1 wherein the step (a) solution is produced by first mixing the carboxamide and paraformaldehyde in substantially equimolar proportions in a solvent quantity of the solvent and heating to about 50° to 100° C. to form a substantially homogeneous solution, then cooling the solution to about 60° C. or below and adding a substantially equimolar proportion of phosphorous acid based on the carboxamide to form said substantially homogeneous solution of said three ingredients.

13. The process of claim 12 wherein the solvent is a mixture consisting essentially of a major proportion of acetonitrile and a minor proportion of acetic acid.

14. The process of claim 13 wherein acetic anhydride is added to said substantially homogeneous solution at a temperature in the range of about 10° to 30° C.

15. The process of claim 14 wherein the resulting solution following the addition of acetic anhydride is heated at a temperature in the range of about 80° to 120° C. for a time effective to result in the formation of an N-acylaminomethylphosphonic acid, RCO—NH—CH$_2$—P(=O)(OH)$_2$, where R is as defined above.

16. A process for the preparation of N-acylaminomethylphosphonic acid having the formula RCO—NH—CH$_2$—P(=O)(OH)$_2$, where R is a non-interfering aliphatic or aromatic radical, which comprises
   (a) forming a first solution of a carboxylic acid anhydride and phosphorous acid in a substantially anhydrous solvent for the anhydride and the acid at a temperature in the range of 10° to about 30° C.;
   (b) forming a substantially homogeneous second solution of substantially equimolar amounts of a carboxamide, RCO—NH$_2$, where R is as defined above, and paraformaldehyde in a substantially anhydrous solvent miscible with the solvent of the first solution;
   (c) mixing the first solution and the second solution at a temperature in the range of about 10° to 30° C. to form a substantially homogeneous reaction mixture;
   (d) heating the reaction mixture at a temperature effective to result in the formation of an N-acylaminomethylphosphonic acid; and
   (e) recovering the N-acylaminomethylphosphonic acid from the reaction mixture.

* * * * *